United States Patent
Deutchman et al.

(10) Patent No.: US 9,523,144 B2
(45) Date of Patent: Dec. 20, 2016

(54) ORTHOPAEDIC IMPLANTS HAVING SELF-LUBRICATED ARTICULATING SURFACES DESIGNED TO REDUCE WEAR, CORROSION, AND ION LEACHING

(75) Inventors: Arnold H. Deutchman, Columbus, OH (US); Robert J. Partyka, Columbus, OH (US); Robert J. Borel, Naples, FL (US)

(73) Assignee: BEAMALLOY RECONSTRUCTIVE MEDICAL PRODUCTS, LLC, Plain City, OH (US)

( * ) Notice: Subject to any disclaimer, the term of this patent is extended or adjusted under 35 U.S.C. 154(b) by 1347 days.

(21) Appl. No.: 12/059,553

(22) Filed: Mar. 31, 2008

(65) Prior Publication Data

US 2008/0221683 A1 Sep. 11, 2008

Related U.S. Application Data

(63) Continuation-in-part of application No. 11/042,150, filed on Jan. 26, 2005, now Pat. No. 7,374,642.
(Continued)

(51) Int. Cl.
*A61F 2/28* (2006.01)
*C23C 14/06* (2006.01)
(Continued)

(52) U.S. Cl.
CPC ........ *C23C 14/0641* (2013.01); *A61F 2/30767* (2013.01); *A61L 27/306* (2013.01);
(Continued)

(58) Field of Classification Search
CPC ............. A61F 2002/30929; A61F 2002/30934
(Continued)

(56) References Cited

U.S. PATENT DOCUMENTS 4,234,972 A * 11/1980 Hench et al. ............... 623/23.57
4,801,300 A * 1/1989 Kurze et al. ............... 623/23.36
(Continued)

OTHER PUBLICATIONS

A. J. Weigand and B. A. Banks: "Ion-beam-sputter modification of the surface morphology of biological implants", J. Vac. Sci. Technol., vol. 14, No. 1, Jan./Feb. 1977, pp. 326-331.

*Primary Examiner* — Brian Pellegrino
(74) *Attorney, Agent, or Firm* — Baker & Hostetler LLP

(57) ABSTRACT

Mechanical devices such as prosthetic knees, hips, shoulders, fingers, elbows, wrists, ankles, fingers and spinal elements when implanted in the body and used as articulating elements are subjected to wear and corrosion. These prosthetic implants are usually fabricated in modular form from combinations of metallic materials such as stainless steels, Co—Cr—Mo alloys, and Ti—Al—V alloys; plastics such as ultra high molecular weight polyethylene (UHMWPE); and ceramics such as alumina and zirconia. As the articulating surfaces of these materials wear and corrode, products including plastic wear debris, metallic wear particles, and metallic ions will be released into the body, transported to and absorbed by bone, blood, the lymphatic tissue, and other organ systems. The polyethylene wear particles have been shown to produce long term bone loss and loosening of the implant. And, even very low concentrations of metallic wear particles and metallic ions are suspect in causing adverse toxic, inflammatory, and immunologic tissue reactions. This invention provides prosthetic implants having articulating surfaces that exhibit a reduced rate of release of wear debris and metal ions into the body and a method of producing such prosthetic implants.

14 Claims, 7 Drawing Sheets

Related U.S. Application Data

(60) Provisional application No. 60/539,996, filed on Jan. 30, 2004.

(51) Int. Cl.

| | |
|---|---|
| *A61F 2/30* | (2006.01) |
| *A61L 27/30* | (2006.01) |
| *C23C 14/08* | (2006.01) |
| *C23C 14/22* | (2006.01) |
| *C23C 14/46* | (2006.01) |
| *C23C 28/04* | (2006.01) |
| *C23C 28/00* | (2006.01) |
| *A61F 2/36* | (2006.01) |
| *A61F 2/38* | (2006.01) |

(52) U.S. Cl.
CPC .......... *C23C 14/081* (2013.01); *C23C 14/225* (2013.01); *C23C 14/46* (2013.01); *C23C 28/00* (2013.01); *C23C 28/042* (2013.01); *C23C 28/044* (2013.01); *C23C 28/046* (2013.01); *A61F 2/3094* (2013.01); *A61F 2/36* (2013.01); *A61F 2/38* (2013.01); *A61F 2002/30929* (2013.01); *A61F 2002/30934* (2013.01); *A61F 2310/00011* (2013.01); *A61F 2310/00592* (2013.01); *A61L 2400/10* (2013.01); *A61L 2400/12* (2013.01); *A61L 2430/02* (2013.01)

(58) Field of Classification Search
USPC .......... 623/23.29, 23.5, 23.36, 23.57, 23.59, 623/23.6, 1.44, 23.53, 23.56, 23.61; 606/76, 606/907; 427/2.24, 2.26, 2.27
See application file for complete search history.

(56) References Cited

U.S. PATENT DOCUMENTS

| | | | |
|---|---|---|---|
| 4,863,810 A | 9/1989 | Bhattacharya et al. | |
| 4,933,058 A | 6/1990 | Bache et al. | |
| 4,944,754 A * | 7/1990 | Linkow et al. | 623/23.6 |
| 4,992,298 A | 2/1991 | Deutchman et al. | |
| 5,055,318 A | 10/1991 | Deutchman et al. | |
| 5,258,028 A | 11/1993 | Ersek et al. | |
| 5,372,660 A * | 12/1994 | Davidson et al. | 148/421 |
| 5,389,195 A | 2/1995 | Ouderkirk et al. | |
| 5,403,592 A | 4/1995 | Hills | |
| 5,482,602 A | 1/1996 | Cooper et al. | |
| 5,520,664 A | 5/1996 | Bricault, Jr. et al. | |
| 5,628,659 A | 5/1997 | Xie et al. | |
| 6,054,185 A | 4/2000 | Inspektor | |
| 6,162,513 A | 12/2000 | Koh et al. | |
| 6,284,377 B1 | 9/2001 | Veerasamy | |
| 6,290,726 B1 * | 9/2001 | Pope et al. | 623/22.15 |
| 6,413,380 B1 | 7/2002 | Pinarbasi | |
| 6,478,931 B1 | 11/2002 | Wadley et al. | |
| 6,613,204 B2 | 9/2003 | Xie et al. | |
| 6,809,066 B2 | 10/2004 | Reade et al. | |
| 7,374,642 B2 | 5/2008 | Deutchman et al. | |
| 2002/0134667 A1 | 9/2002 | Driskell et al. | |
| 2003/0144728 A1* | 7/2003 | Scheuermann et al. | 623/1.44 |
| 2003/0229399 A1* | 12/2003 | Namavar | 623/23.53 |
| 2004/0230301 A1 | 11/2004 | Driskell et al. | |
| 2005/0167261 A1 | 8/2005 | Deutchman et al. | |
| 2005/0182494 A1 | 8/2005 | Schmid | |

\* cited by examiner

| | B. Surface of the IBED coated Co-Cr-Mo pin (EDAX Analysis) Presence of Ca and P cations from the bovine calf serum in the dried remnant of the lubricating film. Also seen are the Al and O peaks from the $Al_2O_3$ coating below the film remnant |

ORTHOPAEDIC IMPLANTS HAVING SELF-LUBRICATED ARTICULATING SURFACES DESIGNED TO REDUCE WEAR, CORROSION, AND ION LEACHING

CROSS REFERENCE TO RELATED APPLICATIONS

This application is a Continuation-in-Part of and claims priority to U.S. patent application Ser. No. 11/042,150, filed on Jan. 26, 2005, now U.S. Pat. No. 7,374,642 titled "TREATMENT PROCESS FOR IMPROVING THE MECHANICAL, CATALYTIC, CHEMICAL, AND BIOLOGICAL ACTIVITY OF SURFACES, AND ARTICLES TREATED THEREWITH," which claims priority to U.S. Provisional Application Ser. No. 60/539,996, filed on Jan. 30, 2004, titled "TREATMENT PROCESS FOR IMPROVING THE MECHANICAL, CATALYTIC, CHEMICAL, AND BIOLOGICAL ACTIVITY OF SURFACES, AND ARTICLES TREATED THEREWITH," the disclosures of which are incorporated herein by reference in their entireties.

FIELD OF THE INVENTION

The present invention relates generally to orthopaedic medicine. More particularly, the present invention relates to an orthopaedic medicine where natural articulating joints such as knees, hips, shoulders, elbows, wrists, ankles, fingers and spinal elements are replaced by implanted mechanical devices to restore diseased or injured skeletal tissue.

BACKGROUND OF THE INVENTION

When mechanical devices such as prosthetic knees, hips, shoulders, fingers, elbows, wrists, ankles, fingers and spinal elements are implanted in the body and used as articulating elements they are subjected to wear and corrosion. These prosthetic (orthopaedic) implants are usually fabricated in modular form with the individual elements manufactured from metallic materials such as stainless steels, Co—Cr—Mo alloys, Zr alloys, and Ti alloys (Ti—Al—V); plastics such as ultra high molecular weight polyethylene (UHMWPE); or ceramics such as alumina and zirconia.

As the articulating surfaces of these orthopaedic implants wear and corrode, products including polyethylene wear particles, metallic wear particles, and metallic ions are typically released into the body. Thereafter, these wear particles may be transported to and absorbed into bone, blood, lymphatic tissue, and other organ systems. In general, these wear particles have adverse effects. For example, the polyethylene wear particles have been shown to produce long-term bone loss and loosening of the implant. In addition, even very low concentrations of metallic wear particles and metallic ions may have adverse immunologic tissue reactions. Accordingly, it is desirable to provide an orthopaedic implant that is capable of overcoming the disadvantages described herein at least to some extent.

SUMMARY OF THE INVENTION

The foregoing needs are met, to a great extent, by the present invention, wherein in one aspect an orthopaedic implant is provided that in some embodiments provides reduced wear and increased fracture and fatigue resistance in comparison with some existing orthopaedic implants.

An embodiment of the present invention pertains to an orthopaedic implant. The orthopaedic implant includes a substrate, nanotextured surface, alloyed case layer, and conformal coating. The nanotextured surface is disposed upon the substrate. The nanotextured surface includes a plurality of bio-active sites. The alloyed case layer is ballistically imbedded on to and below the nanotextured surface. The conformal coating is disposed upon the alloyed case layer. The nanotextured surface, alloyed case layer, and the conformal coating are generated in the presence of a continuous vacuum.

Another embodiment of the present invention relates to an orthopaedic implant. The orthopaedic implant includes a first component and second component. The first component has a first component surface and the second component has a second component surface. The first component and the second component are configured to replace a joint in a patient and the first component surface and the second component surface are configured to mate at an interface. Both the first component and the second component include a substrate, nanotextured surface, alloyed case layer, and conformal coating. The nanotextured surface is disposed upon the substrate. The nanotextured surface includes a plurality of bio-active sites. The alloyed case layer is ballistically imbedded on to and below the nanotextured surface. The conformal coating is disposed upon the alloyed case layer. The nanotextured surface, alloyed case layer, and the conformal coating are generated in the presence of a continuous vacuum.

Yet another embodiment of the present invention pertains to a method of coating a surface of an orthopaedic implant component. In this method, the component is placed into a vacuum chamber. The component has a substrate that is textured to create a nanotextured surface with a plurality of bio-active sites. The bio-active sites are configured to retain a lubricating layer in response to exposure to a bodily fluid and the texturing is accomplished by ion beam sputtering the substrate. In addition, the nanotextured surface is coated so that surface-related properties are made. In this coating step, ions are imbedded into the substrate to generate an alloyed case layer in the substrate and a conformal coating is generated on the alloyed case layer. The texturing and coating steps are performed while maintaining a continuous vacuum in the vacuum chamber.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
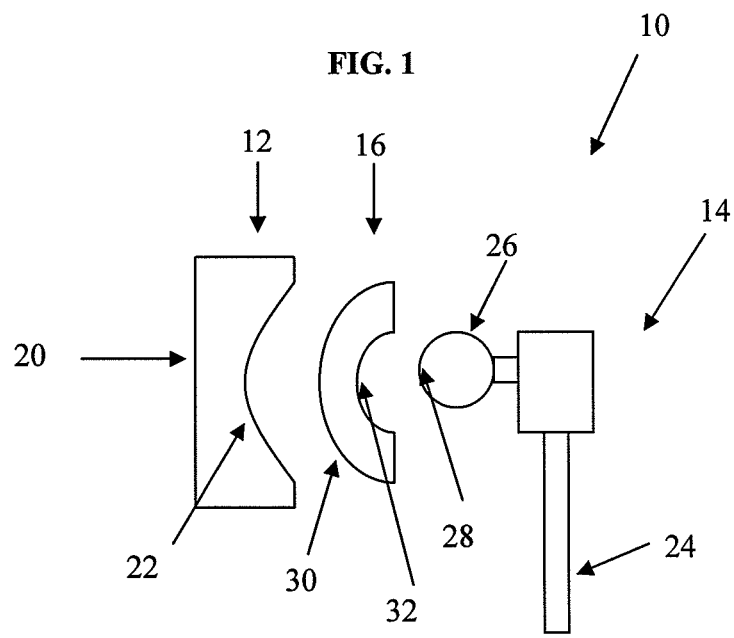
FIG. 1 is a partial cross-sectional front elevation view illustrating a prosthetic hip joint suitable for use with an embodiment of the invention.

The performance of orthopaedic implants 10 of all types and particularly those that provide motion when implanted in the body can be improved dramatically through the use of embodiments of the present invention. The surface treatments described herein may reduce the generation of wear debris, corrosion products, and metal ion leaching when applied to orthopaedic implants 10 of various designs and made from a wide variety of materials. Thus, when so-treated, orthopaedic implants 10 used in patients to restore skeletal motion impaired by injury or disease may reduce or eliminate the osteolysis, inflammatory and toxic response, and carcinogenic effects that can adversely affect conventional implants. This reduction in generation of wear debris is achieved by applying coatings to the articulating counterfaces of the implants that are more wear-resistant, corrosion-resistant, and self lubricating than the various metallic, ceramic, and plastic materials the implants themselves are made from.

According to various embodiments of the invention, surfaces of orthopaedic implants may be treated to reduce wear and improve lubrication. In general, modular orthopaedic implants suitable for use with embodiments of the invention are varied in design and may employ articulating surfaces having different combinations of materials. In some suitable designs, one element may be a metal alloy and the opposed articulating element may be a polymer. In other suitable designs one element may be a metal alloy and the opposed articulating element may be a similar metal alloy. In yet other suitable designs one element may be a ceramic material and the opposed articulating element may be a polymer. And in still another suitable design one element may be a ceramic material and the opposed articulating element may be a similar ceramic material. By treating mating surfaces of the orthopaedic implants as described herein, friction, wear, corrosion, and/or fatigue may be minimized, resulting in a reduced generation of wear debris and metal ion release; and improved lubricity.

Orthopaedic implants treated according to various embodiments of this invention exhibit reduced generation and release of wear particles, corrosion products, and metallic ions into the body. This reduction in non-biologic contaminants results in a reduced inflammatory response of the body to the implant which improves the longevity of the implant residing in the body. The various embodiments of this invention provide an orthopaedic implant that exhibits reduced generation and release of metallic, plastic, and ceramic wear particles; corrosion products; and metallic ions into the body thereby reducing the inflammatory response of the skeletal tissue to the implant. This results in reducing osteolysis leading to loosening of the orthopaedic implant in the bone into which it is implanted, and enhances its longevity.

As described herein, a surface treatment may be applied to either one or both of the articulating opposed surfaces of the implant. The surface treatment provides hardness, wear-resistance and corrosion-resistance, and has self lubricating features that further help reduce the generation and release of wear debris. This surface treatment may be a coating that is initially alloyed into the articulating surfaces of the implant and then grown to a finite dimensional thickness from the alloyed surface. This facilitates relatively greater adhesion of the coating to the articulating surfaces of the implant as compared to conventional coatings. As such, delamination of the coating from the treated articulating surfaces of the implant is reduced or eliminated. In addition, the surface treatment provides a self-lubricating property to further reduce wear between the articulating elements. This is achieved by providing biologically active sites on the surface of the coatings that attract and hold natural lubricants such as synovial fluid or other extracellular fluids present in the tissue around the articulating elements. These fluid retentive surfaces act to provide a continuous thin layer of lubrication between the treated articulating elements which reduces or eliminates physical contact between the surfaces of the elements thus reducing or eliminating the generation and release of metallic, plastic, and ceramic wear debris; corrosion products; and metallic ions into the body.

Conventional case hardening and coating methods often undesirably alter the bulk properties of the materials to which they are applied. Specifically, the hardness, toughness, fracture-resistance, and dimensionality may be altered in an undesirable manner by conventional hardening and coating techniques. Post-coating heat-treatments and/or machining may be employed to return the bulk properties to these conventionally treated articles. However, many materials can not be heat-treated without detrimental effects. Particular examples of materials that can not be heat treated without detrimental effects include: any of the family of stainless steels, Co—Cr—Mo alloys, Ti—Al—V alloys, Zr alloys; alumina and zirconia ceramics; and plastics. It is an advantage of embodiments of the invention that the bulk properties of the implant material are substantially unaffected by surface treatments as described herein. As such, post-coating heat-treating or machining may be avoided.

The coating provided by the various surface treatments described herein may be applied to a metal substrate. These coatings include hard ceramic material such as aluminum oxide ($Al_2O_3$, alpha phase), zirconium oxide ($Zr_2O$), metallic nitrides (such as TiN, $Si_3N_4$, CrN, ZrN, TaN), and/or metallic carbides (such as $Cr_2C$, TiC, WC). The use of these and other hard ceramic materials further reduces abrasion of the coating. In this manner, orthopaedic implants 10 that have high bulk fracture/fatigue-resistant properties characteristic of metallic materials, and also have the high surface wear- and corrosion-resistant properties characteristic of hard ceramic materials may be provided by various embodiments of the invention. This is achieved by applying a ceramic material to the articulating surface of a metallic implant which minimizes the chance of catastrophic failure of the implant due to fracture of the bulk material.

The method of treating one or both of the articulating opposed bearing surfaces of the implant as described herein produces a thin nanocrystalline or nearly-amorphous coating that may include multiple contiguous layers of different materials such as metals (Cr, Ni, Ti, Zr, Al, and others) and hard ceramics such as aluminum oxide ($Al_2O_3$, alpha phase), zirconium oxide ($Zr_2O$), or metallic nitrides (such as TiN, $Si_3N_4$, CrN, ZrN, TaN), or metallic carbides (such as $Cr_2C$, TiC, WC), each grown directly and sequentially from the previously grown layer. In general, this coating process may be carried out at a temperature of 600 degrees Fahrenheit or less. This reduces or eliminates temperature induced changes in bulk properties or dimensions of the treated element. In addition this coating process produces a thin nanocrystalline or nearly-amorphous coating on the articulating surface thereby minimizing the possibility that intergranular cracks or voids in the coating can allow corrosion and subsequent release of metal ions and/or particle wear debris into the patient. Furthermore, this thin nanocrystalline or nearly-amorphous coating on the articulating surface minimizes the possibility that intergranular cracks in the coating can propagate into the underlying substrate to cause it to fail prematurely, as by a fatigue mechanism. It is a further advantage that coating applied as described herein are resistant to the effects of gamma ray sterilization procedures. Thus, the treated implants can sterilized without degrading the wear-resistant, corrosion-resistant, and self-lubricating properties of the treated implant.

The invention will now be described with reference to the drawing figures, in which like reference numerals refer to like parts throughout. FIG. 1 is a partial cross-sectional front elevation view illustrating a prosthetic hip joint 10 suitable for use with an embodiment of the invention. As shown in FIG. 1, the implant 10 is a multi-element modular mechanical construct for attachment to two skeletal members. In general the implant 10 is configured to allow motion between those two skeletal members. The artificial hip is comprised of an acetabular cup 12, femoral component 14, and in some designs an optional liner 16 may be included. The two elements attached to skeletal members include the acetabular cup 12 and femoral component 14. The acetabular cup 12 comprises two surfaces 20 and 22. The surface 20 is fastened to the bony acetabulum of the hip, and the surface 22 is concave in shape and can accept the convex portion of an opposed articulating element. The femoral component 14 includes a stem portion 24 and a spherical portion 26 (the femoral head). The stem portion 24 is inserted into the canal of the femoral bone of the leg and fastened therein. The outside surface 28 of spherical portion 26 of the femoral component 14 is mated to the concave surface 22 of the acetabular cup 12 and is configured to provide articulation between the leg and hip. In this manner, function of a patient's hip may be restored. If included, the liner 16 is interposed between surface 22 and surface 28. In this case the convex surface 30 of element 16 is fastened to the concave surface 22 of the acetabular cup 12, and the concave surface 32 accepts the convex surface 28 of the spherical portion 26. The designs of, and materials chosen for the acetabular cup 12, spherical portion 26 and liner 16 generally determine the nature and rate of generation of the wear debris and products released into the body.

Figure 2:
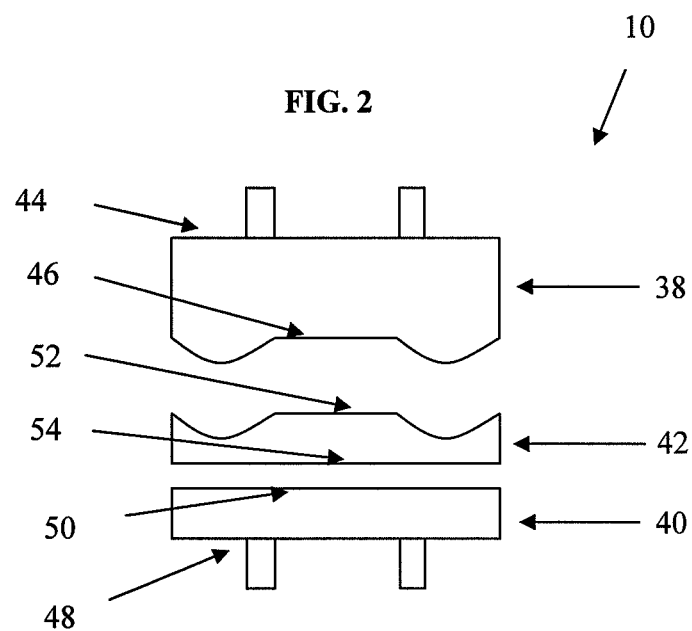
FIG. 2 is an exploded view illustrating a prosthetic knee joint suitable for use with an embodiment of the invention.

FIG. 2 is an exploded view illustrating a prosthetic knee joint suitable for use with an embodiment of the invention. As shown in FIG. 2, the articulating orthopaedic implant 10 may include an artificial knee. The artificial knee includes a femoral condyle 38, tibial plateau 40, and tibial insert 42. The femoral condyle 38 and tibial plateau 40 may be attached to skeletal members of a patient. The femoral condyle 38 includes two surfaces 44 and 46. The surface 44 is fastened to the femoral bone of the leg, and surface 46 is convex in shape and is configured to accept the concave portion of an opposed articulating element such as the tibial insert 42. The tibial plateau 40 includes a bottom surface 48 and a top surface 50. The bottom surface 48 is attached to the top of the tibial bone of the leg and fastened thereon. The tibial insert 42 includes a top surface 52 which is mated to the convex surface 46 and is configured to facilitate articulation of the knee and thereby restore function to the knee. The tibial insert 42 includes a bottom surface 54 which is attached to the top surface 50 of the tibial plateau 40. Left untreated, the designs of, and materials chosen for the elements 38, 40 and 42 will determine the nature and rate of generation of the wear debris and products released into the body.

A variety of combinations of materials are suitable for use with the contacting articulating surfaces of elements in modular orthopaedic hips, knees and other implants according to various embodiments of the invention. These combinations include metal-polymer, ceramic-polymer, metal-metal, and ceramic-ceramic. When treated or coated as described herein, these material combinations reduce friction, wear, and corrosion in modular articulating orthopaedic implants 10. It is an advantage of embodiments of the invention that undesirable particle debris may be reduced or eliminated by the treatments described herein. Particular examples of drawbacks associated with untreated conventional materials are described in Table I and highlight the innovative features of the current invention.

TABLE I

Drawbacks of Conventional Implant Material Combinations

| Material Combination | Typical Materials | Effects |
|---|---|---|
| Metal-Polymer | | |
| Metal | Stainless Steel, Co—Cr—Mo, Ti—Al—V, Zr | Abrasive wear against UHMWPE constantly removes passive oxide layer on the metal which releases metal ions which are potentially toxic and carcinogenic. |
| Polymer | UHMWPE | Adhesive wear releases polymeric particle debris. Fatigue wear releases |

TABLE I-continued

Drawbacks of Conventional Implant Material Combinations

| Material Combination | Typical Materials | Effects |
|---|---|---|
| | | particulate debris, produces fatigue failure fragments, and plastic deformation and cracking of the UHMWPE. Polymeric wear debris and fragments leads to loosening of the implant. |
| Ceramic-Polymer | | |
| Ceramic | Sintered alumina or zirconia | Abrasive wear against UHMWPE less than that seen with metal components. Ceramic wear debris is considered biologically inert |
| Polymer | UHMWPE | Adhesive wear releases polymeric particle debris. Fatigue wear releases particulate debris, produces fatigue failure fragments, and plastic deformation and cracking of the UHMWPE. Polymeric wear debris and fragments leads to loosening of the implant. |
| Metal-Metal | | |
| Metal | Co—Cr—Mo, Ti—Al—V, Zr | Abrasive wear against opposed metallic surface constantly removes passive oxide layer on the metal which releases metal ions which are potentially toxic and carcinogenic. Adhesive wear against opposed metallic surface will produce galling with constant generation of particulate metallic particle debris. |
| Ceramic-Ceramic | | |
| Ceramic | Sintered alumina or zirconia | Wear rate less than seen with metals and ceramic wear debris considered biologically inert. Bulk ceramic materials are brittle and subject to fatigue fracture producing large ceramic fragments and possible catastrophic failure. |

Referring to Table I, it is seen that conventional polymeric materials such as UHMWPE are subject to abrasive, adhesive, and fatigue wear, all of which contribute to the release of polymeric particle debris. In addition the UHMWPE is soft and is subject to bulk plastic deformation and dimensional distortion. The surfaces of metallic components wearing against each other are also subject to abrasive, adhesive and fatigue failure. Abrasive rubbing of opposed metallic surfaces constantly removes passive oxide layers on both metal surfaces which release metal ions that are potentially toxic and carcinogenic. Adhesive wear between the opposed metal surfaces will produce galling and metal transfer with constant generation of particulate metallic particle debris. And under cyclic loading conditions the metal surfaces eventually show fatigue wear. Ceramic materials, when wearing against polymer and metal surfaces exhibit low coefficients of friction and generate relatively low levels of ceramic wear debris. Likewise ceramic elements wearing against each other produce relatively low levels of ceramic wear debris. However, bulk ceramic materials are brittle and subject to fatigue fracture producing large ceramic fragments and possible catastrophic failures.

Figure 3:
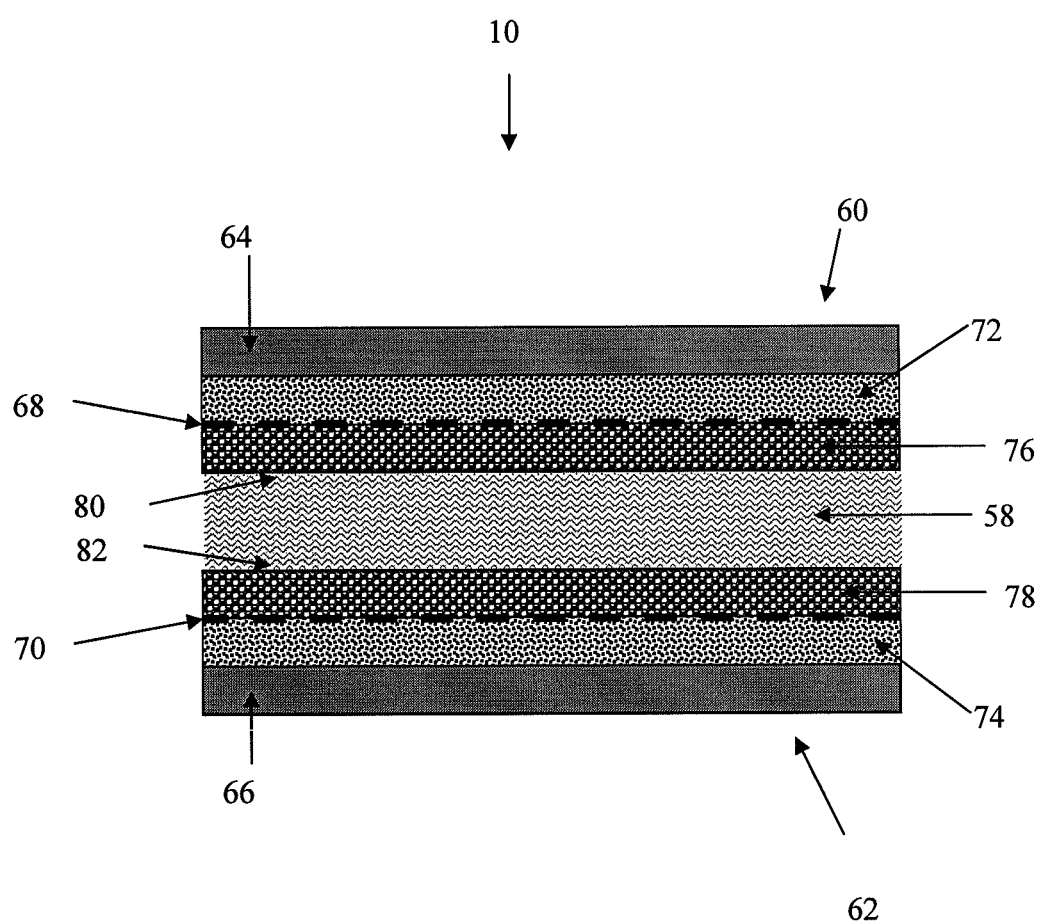
FIG. 3 is a cross-section detail view at an interface of a pair of coated surfaces according to an embodiment of the invention.

FIG. 3 is a cross-section detail view at an interface between two coated surfaces according to an embodiment of the invention. In this embodiment, the articulating orthopaedic implant 10 includes opposed elements that are both fabricated from metallic materials and the counter facing surfaces of both are treated to reduce wear, corrosion, ion leaching, and also to be self-lubricated. As shown in FIG. 3, when installed in a patient, a thin layer of lubrication 58 such as synovial fluid or the like is maintained between surfaces of opposing articulating elements 60 and 62. These opposing articulating elements 60 and 62 may be fabricated from a bulk metal 64 and 66 and both have the bulk hardness and fracture-toughness required for optimum performance and long useful life. In a particular example, the bulk metal 64 and 66 may include Co—Cr—Mo. The original surfaces of both elements are shown at 68 and 70. Using an ion beam enhanced deposition (IBED) process, described herein, a ceramic material is first alloyed into and below the original surfaces 68 and 70 of each opposed element 60 and 62. The presence of ceramic material in the sub-surface alloyed case layers 72 and 74 produces a high concentration of compressive forces in the surfaces which helps convert retained tensile stresses in the surfaces to compressive stresses with a consequent increase in fracture toughness of layers 72 and 74. Sub-surface alloyed case layers 72 and 74 also provide bonding zones from which thicker layers of the ceramic material can be grown as ceramic coatings of finite thickness, 76 and 78. Since ceramic coatings 76 and 78 are grown continuously from sub-surface alloyed case layers 72 and 74, there is no distinct interface between the original surfaces 68 and 70 and the coatings 76 and 78, and thus the ceramic coatings generated by this process are relatively less likely to delaminate from the surfaces 68 and 70 as compared to conventional coatings.

Furthermore, the IBED process allows a high degree of control over the mechanical and metallurgical properties of the ceramic coatings 76 and 78. The metallurgical composition can be maintained in a highly uniform manner throughout the ceramic coatings. As a result, properties such as hardness and wear-resistance can be optimized to reduce or eliminate wear debris generation from the metallic surface beneath the ceramic coating. The coating grain sizes can further be maintained in the nanometer ($1 \times 10^{-9}$ meter) range allowing the coatings to grow substantially void- and pinhole-free thus eliminating corrosion and ion leaching from the metallic surface beneath the ceramic coating. The metallurgical composition can also be tailored to provide biologically active sites on the external surfaces (80 and 82) of the ceramic coating that attract and hold natural lubricants (synovial or other extracellular fluids) present in the tissue around the articulating elements. These fluid retentive surfaces provide a continuously forming thin layer of lubrication 58 between the treated articulating elements that reduces or eliminates physical contact between the surfaces of the elements. In this manner, the generation and release of wear debris, corrosion products, and metallic ions into the body is reduced or eliminated.

The IBED process used to form a ceramic coating in and on the surfaces of the metallic articulating elements proceeds as a continuous, uninterrupted, two-step process described in the following Table II:

TABLE II

| Step 1 (Surface Texturing) | | Step 2 (Coating) | | | |
| --- | --- | --- | --- | --- | --- |
| A | B | A | B | C | D |
| Article placed in vacuum chamber | Surface textured by ion beam sputtering | Coating material evolved and deposited on surface of article | Initial case layer of coating material alloyed into surface of article | Thin conformal coating grown while continuously augmented by ion beam | Thicker coating grown while continuously augmented by ion beam |

Figure 4:
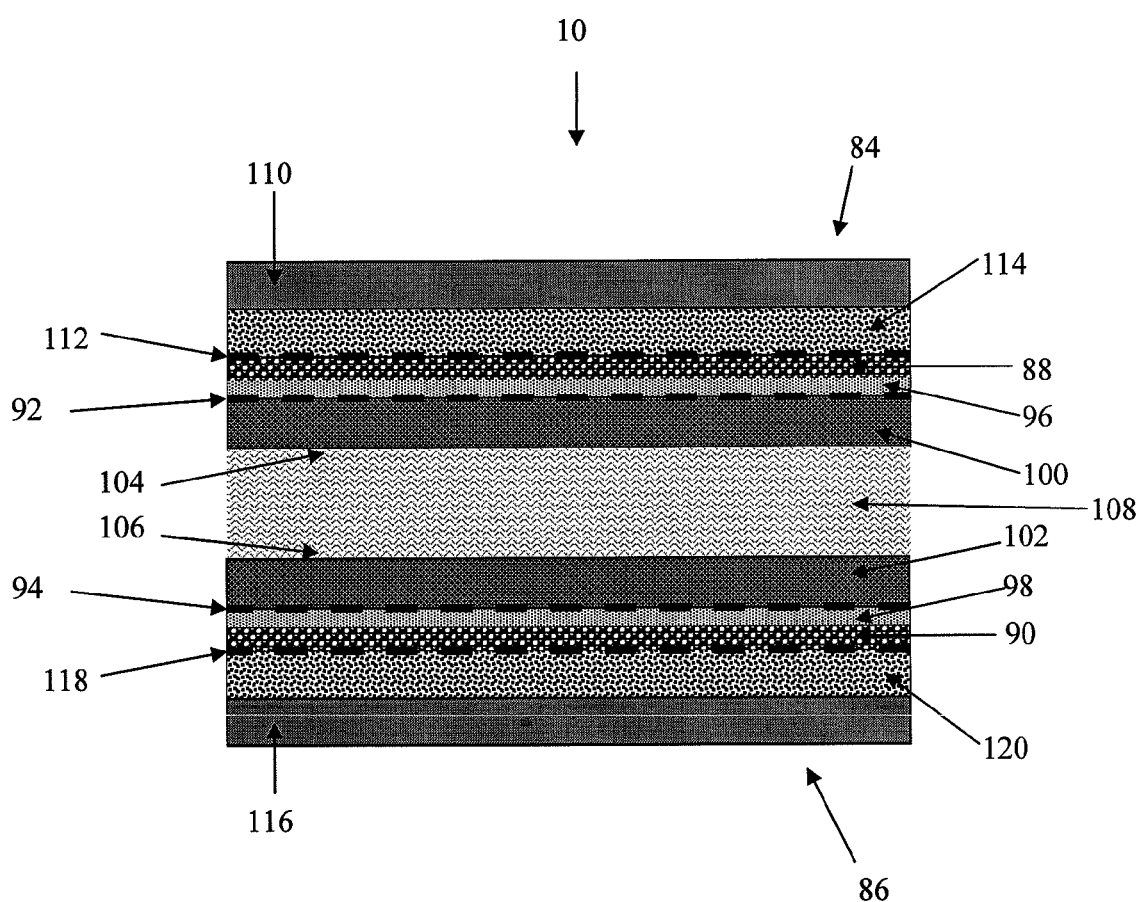
FIG. 4 is a cross-section detail view at an interface of a pair of coated surfaces according to another embodiment of the invention.

FIG. 4 is a cross-section detail view of a coated surface according to another embodiment of the invention. As shown in FIG. 4 the orthopaedic implant 10 includes elements 84 and 86 in close proximity. In this embodiment, a multiple layer coating may be generated in and/or on each articulating surface of the orthopaedic implant 10. This is achieved by performing the IBED process to form a second (outer) coating layer in and out from the surface of the first (inner) layer. Referring to FIG. 4, one or both top surfaces of the coating (88 and 90) previously formed on the articulating surfaces of the orthopaedic implant 10 are shown at 92 and 94. A second material is first alloyed into and below the original surfaces 92 and 94 of the coatings 88 and 90 on each opposed element 84 and 86. Sub-surface alloyed case layers 96 and 98 also provide bonding zones from which thicker layers of the second material can be grown as coatings of finite thickness, 100 and 102. Since the second layer coatings 100 and 102 are grown continuously from sub-surface alloyed case layers 96 and 98, there is no distinct interface between the original surfaces 92 and 94 of the first coating (88 and 90) and the second coatings 100 and 102, and thus the second coatings are relatively less likely to delaminate from the first coatings 88 and 90 as compared to conventional coating procedures. Furthermore, the IBED process allows a high degree of control over the mechanical and metallurgical properties of the second coatings 100 and 102. The metallurgical composition can be maintained highly uniform throughout the second (outer) coating, thus properties like hardness and wear-resistance can be optimized to reduce or eliminate wear debris generation from the metallic surface or first (inner) coating beneath the second (outer) coating. The metallurgical composition can also be tailored to provide biologically active sites on the external surfaces (104 and 106) of the ceramic coating that attract and hold natural lubricants (synovial or other extracellular fluids) present in the tissue around the articulating elements. These fluid retentive surfaces provide a continuously forming thin layer of lubrication 108 between the treated articulating elements which eliminates physical contact between the surfaces of the elements thus eliminating the generation and release of wear debris, corrosion products, and metallic ions into the body.

Figure 5:
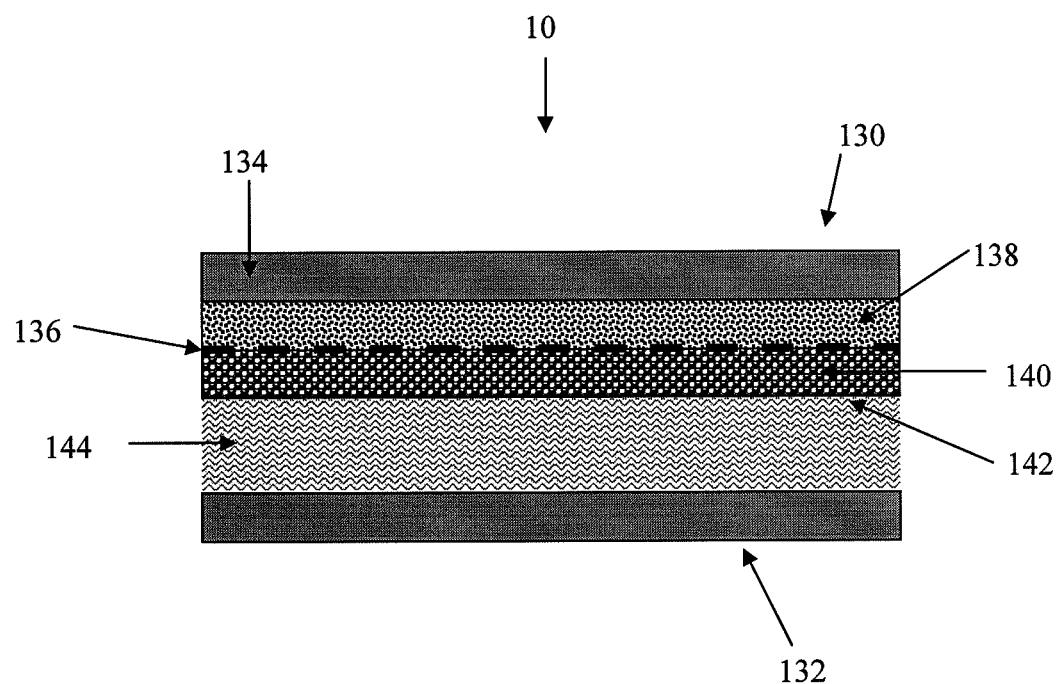
FIG. 5 is a cross-section detail view of a coated surface according to another embodiment of the invention.

FIG. 5 is a cross-section detail view of a coated surfaces according to another embodiment of the invention. As shown in FIG. 5, the articulating opposed element is fabricated from a metallic material and the counter facing opposed element is fabricated from either a plastic or ceramic material, and the surface of only one element is treated to reduce wear, corrosion, ion leaching and also to be self-lubricated.

As shown in FIG. 5, the articulating orthopaedic implant 10 includes opposed elements 130 and 132. In a particular example, the articulating element 130 is fabricated from a bulk metal alloy such as Co—Cr—Mo or Ti—Al—V (134) that has the bulk hardness and fracture-toughness required for optimum performance and long useful life. The counter facing articulating element (132) is fabricated from a bulk plastic or ceramic material. The original surface of the metallic articulating element is shown at 136. Using an IBED process, a ceramic material is first alloyed into and below the original surface 136 of element 130. The presence of ceramic material in the sub-surface alloyed case layer 138 produces a high concentration of compressive forces in the surface which helps convert retained tensile stresses in the surface to compressive stresses with a consequent increase in fracture toughness of layer 138. The sub-surface alloyed case layer 138 also provides a bonding zone from which a thicker layer of the ceramic material can be grown as a ceramic coating 140 of finite thickness. Since the ceramic coating 140 is grown continuously from sub-surface alloyed case layer 138, there is no distinct interface between the original surface 136 and the coating 140, and thus the ceramic coating is less likely to delaminate from the surface 136 as compared to conventional coating methods. Furthermore, the IBED process allows a high degree of control over the mechanical and metallurgical properties of the ceramic coating 140. The metallurgical composition can be maintained highly uniform throughout the ceramic coating, thus properties like hardness and wear-resistance can be optimized to eliminate wear debris generation from the metallic surface beneath the ceramic coating. And coating grain sizes can be maintained in the nanometer ($1\times10^{-9}$ meter) range allowing the coating to grow void- and pinhole-free thus eliminating corrosion and ion leaching from the metallic surface beneath the ceramic coating. The metallurgical composition can also be tailored to provide biologically active sites on the external surface (142) of the ceramic coating that attract and hold natural lubricants (synovial or other extracellular fluids) present in the tissue around the articulating elements. These fluid retentive surfaces provide a continuously forming thin layer of lubrication 144 between the treated and untreated articulating elements that eliminates physical contact between the surfaces of the elements thus reducing or eliminating the generation and release of metallic and plastic or ceramic wear debris, corrosion products, and metallic ions into the body.

The IBED process used to form a ceramic coating in and on the surfaces of the metallic articulating elements proceeds as a continuous, uninterrupted, two-step process is outlined below in Table III:

TABLE III

| Step 1 (Surface Texturing) | | Step 2 (Coating) | | | |
|---|---|---|---|---|---|
| A | B | A | B | C | D |
| Article placed in vacuum chamber | Surface textured by ion beam sputtering | Coating material evolved and deposited on surface of article | Initial case layer of coating material alloyed into surface of article | Thin conformal coating grown while continuously augmented by ion beam | Thicker coating grown while continuously augmented by ion beam |

Figure 6:
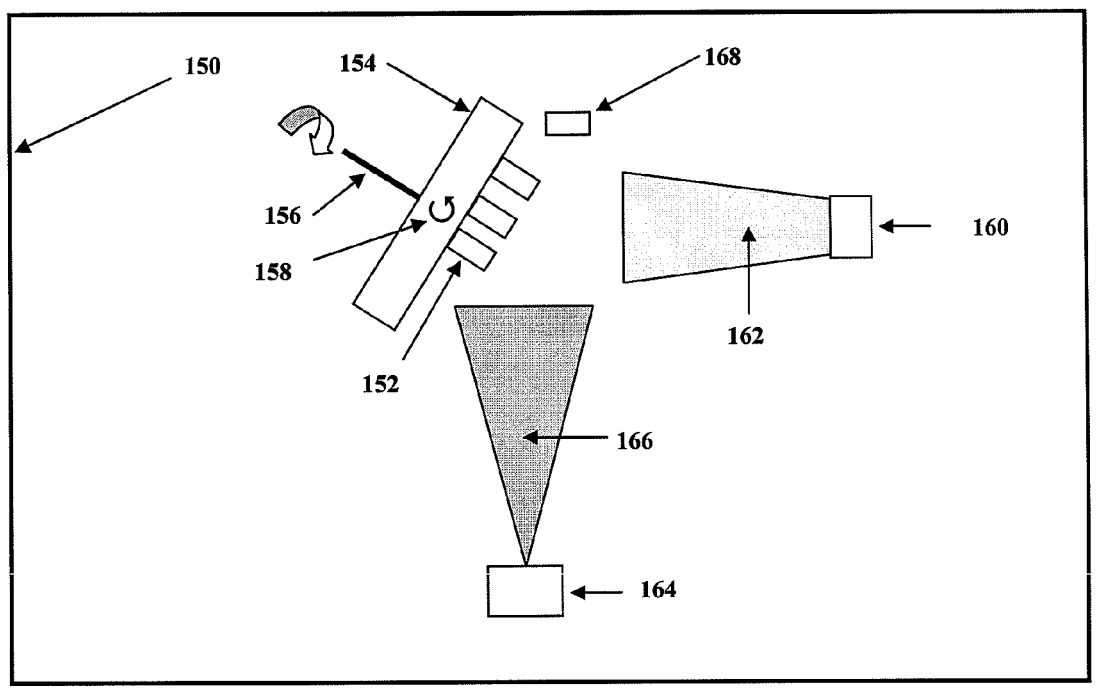
FIG. 6 is a block diagram of a system for coating a surface according to an embodiment of the invention.

FIG. 6 is a block diagram of a system for coating a surface according to an embodiment of the invention. As shown in FIG. 6, the treatment process may be performed in a vacuum vessel 150. A high vacuum environment is preferably maintained in the vacuum vessel 150 in order to allow a high degree of control over the quality of the coating formed in and on the surface of the article. One or more articles 152 may be affixed to a part platen 154. The part platen 154 is configured to provide suitable control of positioning of the articles during the separate cleaning and coating steps. The part platen 154 can rotate about its axis 156 and tilt about its center 158. The tilt angles and rotation rates are chosen such that the surfaces of the parts 152 to be treated are cleaned at the proper angle and the ceramic coating is applied at the proper angle and with good uniformity on the surfaces to be coated. A cleaning/augmenting ion beam source 160 is located within the vacuum chamber and generates a broad beam of cleaning/augmenting ions 162. The broad beam of cleaning/augmenting ions 162 is configured to perform initial cleaning of the surface of the article by sputtering (first step). An electron gun evaporator 164 is located within the vacuum vessel which produces evaporated coating material 166. The coating material 166 is sprayed onto the surface of the articles 152. The electron gun evaporator 164 is configured to contain multiple charges of coating material if a multiple layer coating is to be grown from the articulating surface of the implant. The beam of texturing/augmenting ions 162 is simultaneously applied to the surface of the articles 152 and is used initially to mix the coating material into the surface of the articles 152 forming an alloyed case layer in the surface, and then used to control the composition and crystal structure of the coating as it is grown out from the alloyed case layer (second step).

If multiple layers of coating material are to be applied, the beam of texturing/augmenting 162 ions is simultaneously applied to the surface of the first coating layer and is used initially to mix or ballistically embed the coating material into the surface of the first coating layer forming an alloyed case layer in the first coating layer, and then used to control the composition and crystal structure of the second coating layer as it is grown out from the first coating layer. During both the cleaning and alloying/coating step, the part platen 154 may be rotated about its axis 156 and oscillated about its center 158 to facilitate uniform coverage of the articles. A thickness measuring gauge 168 is positioned near the part platen 154 in order to monitor the arrival of the evaporated coating material 166 and control formation of the alloyed surface layer and then the thicker coating grown from the alloyed surface layer.

Preferably, the two-step treatment process is carried out sequentially in the same vacuum chamber without releasing the high vacuum to atmospheric pressure between steps. If this occurs a latent oxide layer will form on the cleaned surface and will interfere with the formation of the coating. It is also preferable to accurately control the intensities of the cleaning/augmenting ion beam and the angular position of the articles to be treated relative to this directional beam such that the surface alloyed layer and coating are applied uniformly to the surface to be treated.

Embodiments of the invention are further illustrated by the following non-limiting four Examples in which examples of particular coating parameter and test data associated with the coated items is presented.

EXAMPLE 1

Samples of Co—Cr—Mo materials used to manufacture the orthopaedic implants 10 were prepared and coated with a ceramic coating as described herein. The samples were pins and disks utilized in the standard Pin-On-Disk wear test procedure (ASTM F732-00(2006) Standard Test Method for Wear Testing of Polymeric Materials Used in Total Joint Prostheses, American Society For Testing and Materials). The wear of the coated pin and disks was measured and compared to the wear found with uncoated pins and disks manufactured from the same Co—Cr—Mo material.

In this case a two-layer coating was deposited on the pins and disks using the inventive IBED process. The first (inner)

layer was titanium nitride (TiN) and the second (outer) layer was aluminum oxide ($Al_2O_3$). The procedures and processing parameters utilized to deposit the two-layer coating on the pin and disk sample materials are as follows:

TABLE IV

| | Step 1: Surface Texturing | |
|---|---|---|
| | Description | Process Parameters |
| A | Pin & Disk materials placed in vacuum chamber on a rotatable articulated fixture which allows programmed orientation of the device during the process. | Vacuum: 1.0E(−07) Torr |
| B | Surface of the Pin & Disk materials textured by ion beam sputtering with the ion beam from the augmenting ion source and manipulating the materials such that the sputtering angle of incidence is maintained on the surfaces to be textured | Ion Species: N<br>Beam Energy: 1000 eV<br>Beam Current: 4.4 mA/cm$^2$<br>Angle of incidence between 45-75 degrees<br>Part Platen Rotation: 30 RPM<br>Time: 10 minutes |

| | Step 2: Coating by Vacuum Evaporation, TiN first (inner) layer, $Al_2O_3$ second | | |
|---|---|---|---|
| | Description | Process Parameters (TiN) | Process Parameters ($Al_2O_3$) |
| A | E-gun evaporator used to melt and evaporate coating material continuously onto surface of Pin & Disk. | Material: Ti<br>Part platen held at angle between 25 and 75 degrees to evaporator flux<br>Evolution Rate: 14.5 Å/sec<br>Part Platen Rotation: 30 RPM<br>Temperature: <200° F. | Material: $Al_2O_3$<br>Part platen held at angle between 25 and 75 degrees to evaporator flux<br>Evolution Rate: 10 Å/sec<br>Part Platen Rotation: 30 RPM<br>Temperature: 750° F. |
| B | Augmenting ion beam used to alloy the first few layers of the evaporated coating material into device surface of the Pin & Disk thus forming a case layer. | Ion species: N<br>Beam Energy: 1000 eV<br>Beam Current: 4.4 mA/cm$^2$<br>Material: Ti<br>Part platen held at angle between 25 and 75 degrees to evaporator flux<br>Time: 40 seconds<br>Part platen Rotation: 30 RPM<br>Temperature: <200° F. | Ion species: Ar<br>Beam Energy: 1000 eV<br>Beam Current: 2.7 mA/cm$^2$<br>Material: $Al_2O_3$<br>Part platen held at angle between 25 and 75 degrees to evaporator flux<br>Time: 30 seconds<br>Part platen Rotation: 30 RPM<br>Temperature: 750° F. |
| C | Thin conformal coating is grown out from the alloyed case layer as evaporation of the coating material continues. Augmenting ion beam used to control the composition and crystal structure of the coating as it is grown. | Ion species: N<br>Beam Energy: 800 eV<br>Beam Current: 4.4 mA/cm$^2$<br>Material: Ti<br>Part platen held at angle between 25 and 75 degrees to evaporator flux<br>Thickness: 50 Å<br>Part Platen Rotation: 30 RPM<br>Temperature: <200° F. | Ion species: Ar<br>Beam Energy: 800 eV<br>Beam Current: 2.7 mA/cm$^2$<br>Material: $Al_2O_3$<br>Part platen held at angle between 25 and 75 degrees to evaporator flux<br>Thickness: 50 Å<br>Part Platen Rotation: 30 RPM<br>Temperature: 750° F. |
| D | Coating is grown out from the conformal coating as evaporation of the coated material continues. Augmenting ion beam used to control the composition and crystal structure of the coating as it is grown. | Ion species: N<br>Beam Energy: 800 eV<br>Beam Current: 4.4 mA/cm$^2$<br>Material: Ti<br>Part platen held at angle between 25 and 75 degrees to evaporator flux<br>Thickness: 10,000 Å<br>Part Platen Rotation: 30 RPM<br>Temperature: <200° F. | Ion species: Ar<br>Beam Energy: 800 eV<br>Beam Current: 2.7 mA/cm$^2$<br>Material: $Al_2O_3$<br>Part platen held at angle between 25 and 75 degrees to evaporator flux<br>Thickness: 50,000 Å<br>Part Platen Rotation: 30 RPM<br>Temperature: 750° F. |

The test conditions and results of the Pin-On-Disk testing are seen in Table V. In this test, the pin and disk sample materials coated with a two layer $TiN/Al_2O_3$ coating. As a result of a run for 2,000,000 inches of wear travel in the Pin-On-Disk tester a volumetric loss of 0.25 mm³ is shown. This compares to a volumetric loss of 2.1 mm³ measured for 2,000,000 inches of wear travel for uncoated Co—Cr—Mo material.

TABLE V

Comparison of Volumetric Wear Loss (ASTM, F732)

| Sample Material | Load (lbs/in²) | # of Inches | Loss (mm³) |
|---|---|---|---|
| IBED Coated Co—Cr—Mo | 11,700 | 2,000,000 | 0.25 |
| Co—Cr—Mo[1] | 11,700 | 2,000,000 | 2.1 |

[1](R. A. Poggie, "A Review Of The Effects Of Design, Contact Stress, And Materials On The Wear Of Metal-On-Metal Hip Prostheses," from Alternate Bearing Surfaces In Total Joint Replacement, American Society for Testing and Materials, Special Technical Publication STP 1346, 1998)

EXAMPLE 2

A 5 micron thick single layer coating of chromium nitride ($Cr_2N$) was deposited on a 304 stainless steel panel using the inventive process described in U.S. Ser. No. 11/042,150 and then tested for resistance to abrasive wear using a standard Taber Abraser Test. The test was applied using the procedure defined by Military Test Specification (MIL-A-8625F) in which an abrasive wheel (Taber, CS-10), impregnated with 50 micron diameter corundum grits, is rubbed against the coating surface with a loading of 2.2 pounds of force, and run for 10,000 abrasion cycles. The wear loss is measured and presented as the number of microns of coating lost per 10,000 wear cycles.

The procedures and processing parameters utilized to deposit the single layer $Cr_2N$ coating on the 304 stainless steel panel are described in Table VI as follows:

TABLE VI

Step 1: Surface Texturing

| | Description | Process Parameters |
|---|---|---|
| A | Panel material placed in vacuum chamber on a rotatable articulated fixture which allows programmed orientation of the device during the process. | Vacuum: 1.0E(−07) Torr |
| B | Surface of the Panel material textured by ion beam sputtering with the ion beam from the augmenting ion source and manipulating the materials such that the sputtering angle of incidence is maintained on the surfaces to be textured | Ion Species: N<br>Beam Energy: 1000 eV<br>Beam Current: 4.4 mA/cm²<br>Angle of incidence between 45-75 degrees<br>Part Platen Rotation: 30 RPM<br>Time: 10 minutes |

Step 2: Coating by Vacuum Evaporation, $Cr_2N$

| | Description | Process Parameters ($Cr_2N$) |
|---|---|---|
| A | E-gun evaporator used to melt and evaporate coating material continuously onto surface of the Panel. | Material: Cr<br>Part platen held at angle between 25 and 75 degrees to evaporator flux<br>Evolution Rate: 12 Å/sec<br>Part Platen Rotation: 30 RPM<br>Temperature: <200° F. |
| B | Augmenting ion beam used to alloy the first few layers of the evaporated coating material into device surface of the Panel thus forming a case layer. | Ion species: N<br>Beam Energy: 1000 eV<br>Beam Current: 3.4 mA/cm²<br>Material: Cr<br>Part platen held at angle between 25 and 75 degrees to evaporator flux<br>Time: 40 seconds<br>Part platen Rotation: 30 RPM<br>Temperature: <200° F. |
| C | Thin conformal coating is grown out from the alloyed case layer as evaporation of the coating material continues. Augmenting ion beam used to control the composition and crystal structure of the coating as it is grown. | Ion species: N<br>Beam Energy: 800 eV<br>Beam Current: 3.4 mA/cm²<br>Material: Cr<br>Part platen held at angle between 25 and 75 degrees to evaporator flux<br>Thickness: 50 Å<br>Part Platen Rotation: 30 RPM<br>Temperature: <200° F. |
| D | Coating is grown out from the conformal coating as evaporation of the coated material continues. Augmenting ion beam used to control the composition and crystal structure of the coating as it is grown. | Ion species: N<br>Beam Energy: 800 eV<br>Beam Current: 3.4 mA/cm²<br>Material: Cr<br>Part platen held at angle between 25 and 75 degrees to evaporator flux<br>Thickness: 50,000 Å<br>Part Platen Rotation: 30 RPM<br>Temperature: <200° F. |

The result of the Taber Abrasive Wear Testing is seen in Table VII. The IBED $Cr_2N$ coating, showed a loss of 0.15 microns (F) in thickness for the 10,000 cycles of abrasive wear. This compares to a thickness loss of 2.82 microns measured for 10,000 cycles of abrasive wear on uncoated Co—Cr—Mo material with a Rockwell "C" Scale Hardness of 45, that typical of material used for orthopaedic hip and knee implant components.

TABLE VII

Taber Wear Measurement (MIL-A-8625F)

| Material | Abrasive | # of Cycles | Wear (μ) |
|---|---|---|---|
| IBED $Cr_2N$ Coating | CS-10 | 10,000 | 0.15 |
| Co—Cr—Mo ($R_C$ 45) | CS-10 | 10,000 | 2.82 |

EXAMPLE 3

A 5 micron thick single layer coating of aluminum oxide ($Al_2O_3$) was deposited on a 304 stainless steel panel as described herein and then tested for resistance to abrasive wear using a standard Taber Abraser Test. The test was applied using the procedure defined by Military Test Specification (MIL-A-8625F) in which an abrasive wheel (Taber, CS-10), impregnated with 50 micron diameter corundum grits, is rubbed against the coating surface with a loading of 2.2 pounds of force, and run for 10,000 abrasion cycles. The wear loss is measured and presented as the number of microns of coating lost per 10,000 wear cycles.

The procedures and processing parameters utilized to deposit the single layer $Al_2O_3$ coating on the 304 stainless steel panel are illustrated in Table VIII as follows:

TABLE VIII

| | Step 1: Surface Texturing | |
|---|---|---|
| | Description | Process Parameters |
| A | Panel material placed in vacuum chamber on a rotatable articulated fixture which allows programmed orientation of the device during the process. | Vacuum: 1.0E(−07) Torr |
| B | Surface of the Panel material textured by ion beam sputtering with the ion beam from the augmenting ion source and manipulating the materials such that the sputtering angle of incidence is maintained on the surfaces to be textured | Ion Species: Ar<br>Beam Energy: 1000 eV<br>Beam Current: 4.4 mA/cm$^2$<br>Angle of incidence between 45-75 degrees<br>Part Platen Rotation: 30 RPM<br>Time: 10 minutes |

| | Step 2: Coating by Vacuum Evaporation, $Al_2O_3$ | |
|---|---|---|
| | Description | Process Parameters ($Al_2O_3$) |
| A | E-gun evaporator used to melt and evaporate coating material continuously onto surface of the Panel. | Material: $Al_2O_3$<br>Part platen held at angle between 25 and 75 degrees to evaporator flux<br>Evolution Rate: 12 Å/sec<br>Part Platen Rotation: 30 RPM<br>Temperature: <200° F. |
| B | Augmenting ion beam used to alloy the first few layers of the evaporated coating material into device surface of the Panel thus forming a case layer. | Ion species: Ar<br>Beam Energy: 1000 eV<br>Beam Current: 2.7 mA/cm$^2$<br>Material: $Al_2O_3$<br>Part platen held at angle between 25 and 75 degrees to evaporator flux<br>Time: 40 seconds<br>Part platen Rotation: 30 RPM<br>Temperature: <200° F. |
| C | Thin conformal coating is grown out from the alloyed case layer as evaporation of the coating material continues. Augmenting ion beam used to control the composition and crystal structure of the coating as it is grown. | Ion species: Ar<br>Beam Energy: 800 eV<br>Beam Current: 2.7 mA/cm$^2$<br>Material: $Al_2O_3$<br>Part platen held at angle between 25 and 75 degrees to evaporator flux<br>Thickness: 50 Å<br>Part Platen Rotation: 30 RPM<br>Temperature: <200° F. |
| D | Coating is grown out from the conformal coating as evaporation of the coated material continues. Augmenting ion beam used to control the composition and crystal structure of the coating as it is grown. | Ion species: Ar<br>Beam Energy: 800 eV<br>Beam Current: 2.7 mA/cm$^2$<br>Material: $Al_2O_3$<br>Part platen held at angle between 25 and 75 degrees to evaporator flux<br>Thickness: 50,000 Å<br>Part Platen Rotation: 30 RPM<br>Temperature: <200° F. |

The result of the Taber Abrasive Wear Testing is seen in Table IX. The IBED $Al_2O_3$ coating, showed a loss of 0.07 microns (μ) in thickness for the 10,000 cycles of abrasive wear. This compares to a thickness loss of 2.82 microns measured for 10,000 cycles of abrasive wear on uncoated Co—Cr—Mo material with a Rockwell "C" Scale Hardness of 45, that typical of material used for orthopaedic hip and knee implant components.

TABLE IX

| Taber Wear Measurement (MIL-A-8625F) | | | |
|---|---|---|---|
| Material | Abrasive | # of Cycles | Wear (μ) |
| IBED $Al_2O_3$ Coating | CS-10 | 10,000 | 0.07 |
| Co—Cr—Mo ($R_C$ 45) | CS-10 | 10,000 | 2.82 |

EXAMPLE 4

Pin and disk samples were prepared from Co—Cr—Mo material used to manufacture orthopaedic implants, and then coated with a ceramic coating as described herein in order to test the fluid retentive properties of the deposited ceramic. In this case a two-layer coating was deposited on the Co—Cr—Mo pin and disk using the inventive IBED process. The first (inner) layer was titanium nitride (TiN) and the second (outer) layer was aluminum oxide ($Al_2O_3$). The procedures and processing parameters utilized to deposit the two-layer coating on the Co—Cr—Mo pin and disk samples are illustrated in Table X as follows:

TABLE X

| | Step 1: Surface Texturing | |
|---|---|---|
| | Description | Process Parameters |
| A | Pin & Disk materials placed in vacuum chamber on a rotatable articulated fixture which allows programmed orientation of the device during the process. | Vacuum: 1.0E(−07) Torr |
| B | Surface of the Pin & Disk materials textured by ion beam sputtering with the ion beam from the augmenting ion source and manipulating the materials such that the sputtering angle of incidence is maintained on the surfaces to be textured | Ion Species: N<br>Beam Energy: 1000 eV<br>Beam Current: 4.4 mA/cm$^2$<br>Angle of incidence between 45-75 degrees<br>Part Platen Rotation: 30 RPM<br>Time: 10 minutes |

| | Step 2: Coating by Vacuum Evaporation, TiN first (inner) layer, $Al_2O_3$ second | | |
|---|---|---|---|
| | Description | Process Parameters (TiN) | Process Parameters ($Al_2O_3$) |
| A | E-gun evaporator used to melt and evaporate coating | Material: Ti<br>Part platen held at angle between 25 and 75 | Material: $Al_2O_3$<br>Part platen held at angle between 25 and 75 degrees to |

TABLE X-continued

| | material continuously onto surface of Pin & Disk. | degrees to evaporator flux Evolution Rate: 14.5 Å/sec Part Platen Rotation: 30 RPM Temperature: <200° F. | evaporator flux Evolution Rate: 10 Å/sec Part Platen Rotation: 30 RPM Temperature: 750° F. |
|---|---|---|---|
| B | Augmenting ion beam used to alloy the first few layers of the evaporated coating material into device surface of the Pin & Disk thus forming a case layer. | Ion species: N Beam Energy: 1000 eV Beam Current: 4.4 mA/cm² Material: Ti Part platen held at angle between 25 and 75 degrees to evaporator flux Time: 40 seconds Part platen Rotation 30 RPM Temperature: <200° F. | Ion species: Ar Beam Energy: 1000 eV Beam Current: 2.7 mA/cm² Material: $Al_2O_3$ Part platen held at angle between 25 and 75 degrees to evaporator flux Time: 30 seconds Part platen Rotation: 30 RPM Temperature: 750° F. |
| C | Thin conformal coating is grown out from the alloyed case layer as evaporation of the coating material continues. Augmenting ion beam used to control the composition and crystal structure of the coating as it is grown. | Ion species: N Beam Energy: 800 eV Beam Current: 4.4 mA/cm² Material: Ti Part platen held at angle between 25 and 75 degrees to evaporator flux Thickness: 50 Å Part Platen Rotation: 30 RPM Temperature: <200° F. | Ion species: Ar Beam Energy: 800 eV Beam Current: 2.7 mA/cm² Material: $Al_2O_3$ Part platen held at angle between 25 and 75 degrees to evaporator flux Thickness: 50 Å Part Platen Rotation: 30 RPM Temperature: 750° F. |
| D | Coating is grown out from the conformal coating as evaporation of the coated material continues. Augmenting ion beam used to control the composition and crystal structure of the coating as it is grown. | Ion species: N Beam Energy: 800 eV Beam Current: 4.4 mA/cm² Material: Ti Part platen held at angle between 25 and 75 degrees to evaporator flux Thickness: 10,000 Å Part Platen Rotation: 30 RPM Temperature: <200° F. | Ion species: Ar Beam Energy: 800 eV Beam Current: 2.7 mA/cm² Material: $Al_2O_3$ Part platen held at angle between 25 and 75 degrees to evaporator flux Thickness: 50,000 Å Part Platen Rotation: 30 RPM Temperature: 750° F. |

An additional set of pin-on-disk samples was prepared from solid, single crystal, alpha phase $Al_2O_3$. The counter facing surfaces of this pin-on-disk set would not have the same surface nanostructure, and thus fluid-retentive properties, as would the $Al_2O_3$ coating deposited on the Co—Cr—Mo samples using the inventive process.

Both sample pin and disk sets were tested according to the standard pin-on-disk wear test procedure (ASTM F732-00 (2006) "Standard Test Method for Wear Testing of Polymeric Materials Used in Total Joint Prostheses, American Society for Testing and Materials"). The samples were immersed in defined bovine calf serum as a lubricant (Hyclone Labs: Cat. No. SH30073.04) during the entirety of the test. After completion of 2,000,000 cycles in the pin-on-disk test, both sample sets were carefully dried and the surface the pins imaged using scanning electron microscopy (SEM), and the surface composition analyzed with energy dispersive X-ray analysis (EDAX).

Figure 7:
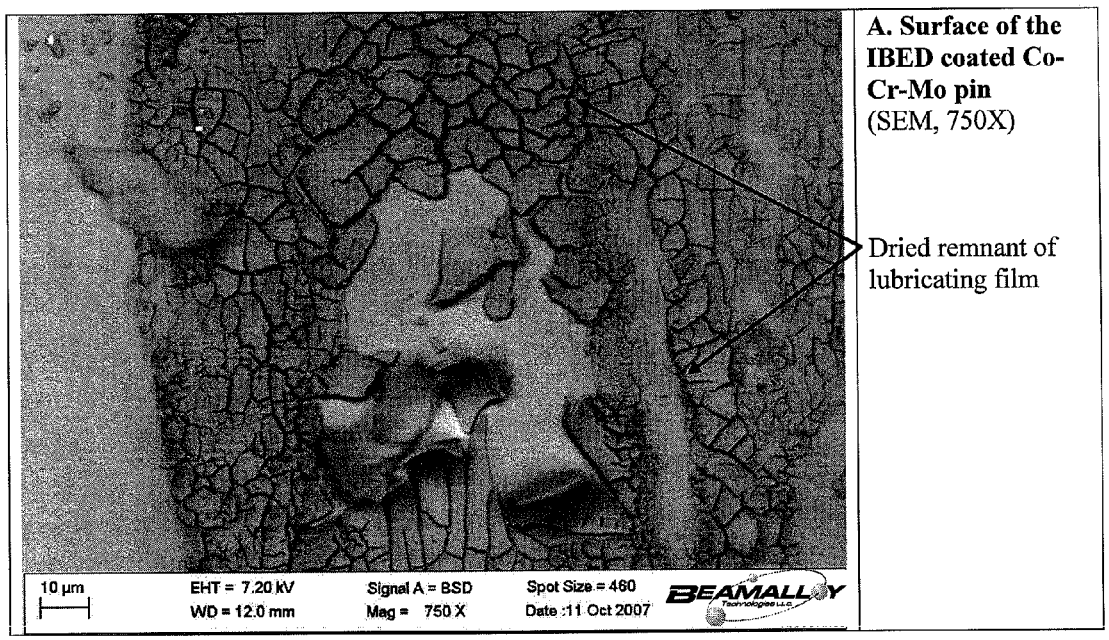
FIG. 7, is a scanning electron micrograph image of a test pin surface showing remnants of a lubricating film adhered to the surface of an $Al_2O_3$ coating.
Figure 8:
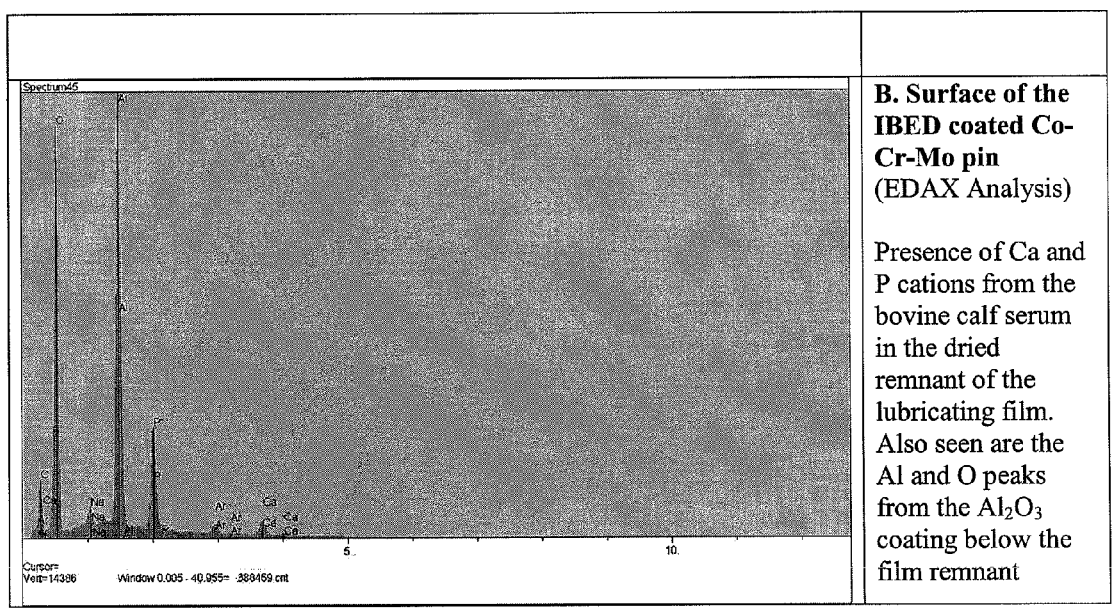
FIG. 8 is an energy dispersive X-ray analysis showing the presence of both calcium and phosphorus cations.

No residue was detected by either SEM imaging or EDAX analysis on the surface of the single crystal, alpha phase, pin indicating that the surface of the solid $Al_2O_3$ pin did not have the properties of a fluid-retentive surface. The IBED-coated Co—Cr—Mo pin surface did however show remnants of a film that had been retained on the surface of the $Al_2O_3$ coating. FIG. 7, is a scanning electron micrograph image of the pin surface showing remnants of the lubricating film still adhered to the surface of the $Al_2O_3$ coating. FIG. 8 is an energy dispersive X-ray analysis showing the presence of both Ca and P cations which are inorganic elements present in the defined bovine calf serum proteins. Thus it is confirmed that the structure and surface activity of $Al_2O_3$ coatings as deposited by the inventive IBED process acts as a fluid retentive surface which maintains the self-lubricating performance of orthopaedic implants so-treated.

CONCLUSIONS

The orthopaedic implants 10 with surface treatments provided by this invention will generate less debris in the form of wear products, corrosion products, and metallic ion leaching which are liberated and transported to bone, blood, the lymphatic system, and other internal organs. This will result in less inflammation, toxicity, and immune response resulting in increased longevity of the orthopaedic implant 10 and less adverse effects on the patient. The surface treatments can be applied to a variety of the materials used to fabricate the articulating elements of the modular orthopaedic implants 10, and are useful for a variety of combinations of metal, ceramic, and polyethylene articulating elements.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An orthopaedic implant comprising:
   a first component, the first component having a first component surface; and
   a second component, the second component having a second component surface, wherein the first component and the second component are configured to replace a joint in a patient and the first component surface and the second component surface are configured to mate at an interface, wherein both the first component and the second component include:
   a metal substrate selected from the group consisting of stainless steels, Co—Cr—Mo alloys, Zr alloys, and Ti alloys;
   a nanotextured surface disposed directly upon the metal substrate having surface features in a size of 10-9 meters;
   a ceramic coating selected from the group consisting of: $Al_2O_3$ (alpha phase), zirconium oxide ($Zr_2O$); metallic nitrides; and metallic carbides conforming to the nanotextured surface and including a plurality of bio-active sites configured to attract and retain calcium and phosphorous cations; and
   a transition zone disposed between the metal substrate and the ceramic coating, wherein the transition zone includes a concentration gradient transitioning from the metal substrate to the ceramic coating and wherein there is no distinct interface between the metal substrate and the ceramic coating.

2. The orthopaedic implant according to claim 1, wherein the nanotextured surface is configured to improve lubricity of the orthopaedic implant in the presence of bodily fluids.

3. The orthopaedic implant according to claim 2, wherein the plurality of bio-active sites are configured to improve lubricity of the orthopaedic implant by retaining calcium and phosphorous cations from synovial fluid upon the nanotextured surface.

4. The orthopaedic implant according to claim 1, wherein the ceramic coating is imbedded to a depth of about 5 nanometers below the nanotextured surface.

5. The orthopaedic implant according to claim 1, wherein a grain structure of the ceramic coating is substantially amorphous.

6. The orthopaedic implant according to claim 1, wherein the nanotextured surface is generated with a directional ion beam sputtering device.

7. The orthopaedic implant according to claim 1, wherein the ceramic coating is generated with an ion beam enhanced deposition (IBED) process.

8. An orthopaedic implant to replace a joint in a patient, the orthopaedic implant comprising:
   a first component having a first component surface; and
   a second component having a second component surface, wherein the first component and the second component are selected from the group consisting of: an acetabular cup; a femoral component; a femoral condyle; a tibial plateau; and a tibial insert, wherein the second component surface is selected from the group consisting of: a metal; a ceramic; and an ultra high molecular weight polymer, wherein the first component surface and the second component surface are configured to mate at an interface, wherein the first component surface includes:
   a metal substrate selected from the group consisting of stainless steels, Co—Cr—Mo alloys, Zr alloys, and Ti alloys;
   a nanotextured surface disposed directly upon the metal substrate having surface features in a size of 10-9 meters;
   a ceramic coating selected from the group consisting of: $Al_2O_3$ (alpha phase), zirconium oxide ($Zr_2O$); silicon nitride ($Si_3N_4$), metallic nitrides; and metallic carbides conforming to the nanotextured surface and including a plurality of bio-active sites configured to attract and retain calcium and phosphorous cations; and
   a transition zone disposed between the metal substrate and the ceramic coating, wherein the transition zone includes a concentration gradient transitioning from the metal substrate to the ceramic coating and wherein there is no distinct interface between the metal substrate and the ceramic coating.

9. The orthopaedic implant according to claim 8, wherein the nanotextured surface is configured to improve lubricity of the orthopaedic implant in the presence of bodily fluids.

10. The orthopaedic implant according to claim 9, wherein the plurality of bio-active sites are configured to improve lubricity of the orthopaedic implant by retaining calcium and phosphorous cations from synovial fluid upon the nanotextured surface.

11. The orthopaedic implant according to claim 8, wherein the ceramic coating is imbedded to a depth of about 5 nanometers below the nanotextured surface.

12. The orthopaedic implant according to claim 8, wherein a grain structure of the ceramic coating is substantially amorphous.

13. The orthopaedic implant according to claim 8, wherein the nanotextured surface is generated with a directional ion beam sputtering device.

14. The orthopaedic implant according to claim 8, wherein the ceramic coating is generated with an ion beam enhanced deposition (IBED) process.

* * * * *